(12) United States Patent
Oesterreich

(10) Patent No.: US 9,203,227 B2
(45) Date of Patent: Dec. 1, 2015

(54) DEVICE FOR GUIDING A CABLE IN A MEDICAL DOSING APPARATUS, DOSING DEVICE, TREATMENT APPARATUS, AS WELL AS METHOD

(75) Inventor: Stefan Oesterreich, Neu-Anspach (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 600 days.

(21) Appl. No.: 13/362,095

(22) Filed: Jan. 31, 2012

(65) Prior Publication Data

US 2012/0193279 A1    Aug. 2, 2012

Related U.S. Application Data

(60) Provisional application No. 61/437,699, filed on Jan. 31, 2011.

(30) Foreign Application Priority Data

Jan. 31, 2011    (DE) .......................... 10 2011 009 909

(51) Int. Cl.
*A61M 1/16*    (2006.01)
*A61M 1/14*    (2006.01)
(Continued)

(52) U.S. Cl.
CPC ............... *H02G 11/00* (2013.01); *A61M 1/16* (2013.01); *A61M 5/1413* (2013.01); *A61M 5/14216* (2013.01); *A61M 1/14* (2013.01)

(58) Field of Classification Search
CPC ......... B01D 61/30; B01D 61/32; A61M 1/14; A61M 1/16; A61M 5/00; A61M 5/14; A61M 5/1413; A61M 5/168; A61M 5/31; A61M 5/34; A61M 25/01; A61M 39/10; A61M 39/12; A61M 5/178; A61M 5/1782; A61M 5/20; A61M 5/315; A61M 5/31576; A61M 5/31578; A61M 2005/2006; A61M 2005/2026; A61M 5/142; A61M 5/14212; A61M 5/14216; A61M 5/142; A61M 5/1422; A61M 5/145; A61M 5/1452; A61M 5/165; A61M 5/1657; A61M 5/2006
USPC .................. 210/85, 91, 321.6, 541, 645, 646; 604/5.01, 6.01, 6.09, 19, 21, 27, 93.01, 604/95.01, 131, 174–177, 204, 264, 273, 604/523, 528, 533, 534, 187–197
See application file for complete search history.

(56) References Cited

U.S. PATENT DOCUMENTS 2,295,849 A * 9/1942 Kayden .......................... 604/136
3,702,608 A * 11/1972 Tibbs ............................. 604/136
(Continued)

FOREIGN PATENT DOCUMENTS

DE    37 44 749 C1    4/1989
DE    199 06 409 B4    8/2000
(Continued)

OTHER PUBLICATIONS

PCT International Search Report from PCT/EP2012/000368, mailed on May 18, 2012.

*Primary Examiner* — Joseph Drodge
(74) *Attorney, Agent, or Firm* — Kenyon & Kenyon LLP

(57) ABSTRACT

The invention pertains to a device for guiding at least one cable for use in a medical dosing apparatus, which features at least one movable section, characterized in that the device is connected or at least designed to be connected to the at least one movable section of the dosing apparatus permitting movement in tandem. It pertains further to a dosing apparatus, a treatment apparatus, a method for position detection as well as a method to enable or carry out position detection.

15 Claims, 4 Drawing Sheets

(51) Int. Cl.
  *B01D 61/30* (2006.01)
  *B01D 61/32* (2006.01)
  *A61M 5/00* (2006.01)
  *A61M 5/14* (2006.01)
  *A61M 5/20* (2006.01)
  *H02G 11/00* (2006.01)
  *A61M 5/142* (2006.01)

(56) References Cited

U.S. PATENT DOCUMENTS

| | | | | |
|---|---|---|---|---|
| 4,617,016 | A * | 10/1986 | Blomberg | 604/155 |
| 5,195,985 | A * | 3/1993 | Hall | 604/195 |
| 5,338,311 | A * | 8/1994 | Mahurkar | 604/195 |
| 5,441,636 | A * | 8/1995 | Chevallet et al. | 210/232 |
| 5,690,618 | A * | 11/1997 | Smith et al. | 604/232 |
| 5,989,213 | A * | 11/1999 | Maginot | 604/28 |
| 6,210,362 | B1 * | 4/2001 | Ponzi | 604/95.01 |
| 6,595,962 | B1 * | 7/2003 | Perthu | 604/187 |
| 8,075,531 | B2 * | 12/2011 | Davey | 604/175 |
| 8,617,116 | B2 * | 12/2013 | Davey | 604/175 |
| 2004/0020675 | A1 | 2/2004 | Bally et al. | |
| 2005/0059925 | A1 * | 3/2005 | Maginot et al. | 604/43 |
| 2005/0096609 | A1 * | 5/2005 | Maginot et al. | 604/271 |
| 2005/0234382 | A1 | 10/2005 | Tonelli et al. | |
| 2007/0175828 | A1 * | 8/2007 | Goedje et al. | 210/646 |
| 2007/0240817 | A1 * | 10/2007 | Strong et al. | 156/304.3 |
| 2008/0051711 | A1 * | 2/2008 | Mounce et al. | 604/131 |
| 2008/0306443 | A1 | 12/2008 | Neer et al. | |
| 2014/0058214 | A1 * | 2/2014 | Woodward | 600/301 |
| 2014/0163664 | A1 * | 6/2014 | Goldsmith | 623/1.11 |

FOREIGN PATENT DOCUMENTS

| | | |
|---|---|---|
| DE | 699 36 014 T2 | 1/2008 |
| DE | 10 2006 039 525 A1 | 2/2008 |
| DE | 10 2009 018 283 A1 | 12/2010 |
| EP | 0962191 B1 | 5/2007 |
| EP | 1 066 846 A1 | 10/2007 |
| WO | 99/54651 A1 | 10/1999 |

* cited by examiner

DEVICE FOR GUIDING A CABLE IN A MEDICAL DOSING APPARATUS, DOSING DEVICE, TREATMENT APPARATUS, AS WELL AS METHOD

CROSS-REFERENCE TO RELATED APPLICATIONS

The present application claims priority to, and the benefit of, U.S. Provisional Application 61/437,699 filed on Jan. 31, 2011. The contents of this provisional application is incorporated herein by reference in its entirety. The present application also claims priority to, and the benefit of, German Patent Application DE 10 2011 009 909.3 filed on Jan. 31, 2011. The contents of this foreign application is incorporated herein by reference in its entirety.

FIELD OF THE INVENTION

The present invention relates to a device for guiding a cable or a conductor. It further relates to a dosing apparatus, a treatment apparatus, and methods for position detection.

BACKGROUND OF THE INVENTION

In medical apparatuses, components are regularly used that require an external power supply or need a signal connection external to the apparatus, connected by a conductor. This signal or power connection is in many cases provided by means of a cable.

One object of the present invention is to propose a device for guiding at least one cable or an otherwise formed conductor, hereafter also shortly referred to as the device according to the present invention, for use in a medical dosing apparatus, hereafter also shortly referred to as a dosing apparatus.

SUMMARY OF THE INVENTION

The device according to the present invention is interconnected so as to be movable with at least one movable section of the dosing apparatus; alternatively the device according to the present invention is hereby designed for such a movable connection.

The connection enables a movement of the device together with the movable section of the dosing apparatus. Thus the device and the movable section will move together, at the least they are designed for such a combined movement.

The dosing apparatus according to the present invention is designed for use with the device according to the present invention for guiding a cable or offers at least one such device.

The treatment apparatus according to the present invention displays at least one dosing apparatus according to the present invention and/or at least one device according to the present invention, or is herewith respectively connected.

The present invention provides a method for detecting the position of a movable section of a dosing apparatus. It comprises the use of at least one device according to the present invention.

The present invention also provides a method to enable or accomplish a detection of the position of a movable section of a dosing apparatus relative to at least one non-movable section of the dosing apparatus. This method comprises at least the positioning of at least one sensor on the movable section and the guidance of a cable connected to the sensor, by means of at least one device according to the present invention.

DETAILED DESCRIPTION OF THE INVENTION

Figure 1:
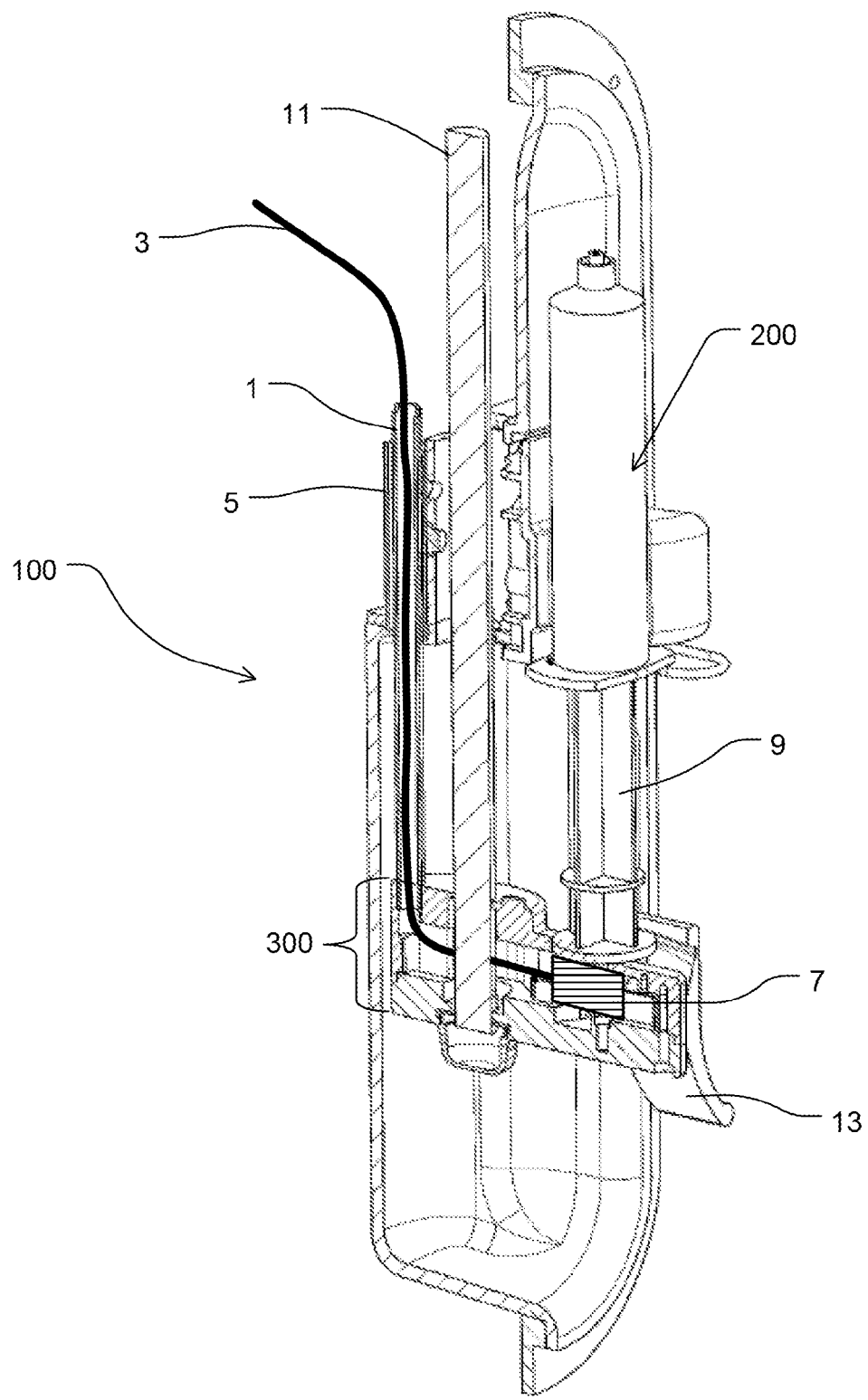
FIG. 1 shows a sectional view of a dosing apparatus according to the present invention with a device according to the present invention for guiding a cable.

Embodiments according to the present invention can display one or more of the features designated in the following.

In all the embodiments it is to be understood that the use of the terms can be and can have and so on are synonymous with is/are preferably and has/have preferably, respectively, and shall describe specific embodiments according to the present invention.

A cable is in specific embodiments of the present invention a conductor. Both terms are to be understood as synonymous in the following wherever this makes sense to a person skilled in the art.

In some embodiments according to the present invention, the cable or conductor is an electrical conductor to supply electrical components with power. The conductor can be single or multi-core. The conductor can feature or be a braid or stranded wire or litz wire.

In specific embodiments, the electrical conductor is covered with an insulator, for example a plastic covering or an insulating sleeve.

In specific embodiments, the cable serves for the transmission of signals, for example for transmitting digital power signals.

In specific embodiments according to the present invention, the cable is an optical conductor or at least features one such.

The term guiding a cable as used here in specific embodiments, describes the housing or passing of a cable as in, for example, cable ducts or cable trunkings.

The term guiding a cable as used here in specific embodiments describes the positioning, gathering, holding up or supporting the cable.

The term guiding a cable as used here in several embodiments, denotes the taking along of the cable in a movement which is performed by the device according to the present invention.

A medical dosing apparatus is in specific embodiments an apparatus for dosing liquids, medical solutions, infusions and so on.

In specific embodiments according to the present invention, the dosing apparatus exhibits at least one holding chamber for the substance or solution to be dosed, e.g., in the form of a variable volume syringe, a support device for the holding chamber, a movable section as well as at least one device according to the present invention for guiding at least one cable.

In some embodiments, the medical dosing apparatus according to the present invention additionally exhibits at least one electrical component—as for example an electrically powered sensor—and/or a positioning element for moving the movable section.

The positioning element is, in specific embodiments according to the present invention, a moving tube. In some embodiments according to the present invention, the positioning element revolves around its own longitudinal axis during movement of the movable section.

The holding chamber is in some embodiments a—in most cases cylindrical—cavity with a movable piston arranged within, also known as a plunger, as well as an orifice or opening to allow the output of the contents of the holding chamber. The filling of the holding chamber can be accomplished through various means; it can for example be filled by the doctor or during production.

In some embodiments, the holding chamber is made of plastic.

The holding chamber can be a conventional pharmaceutical syringe.

The holding chamber can be formed as a single-use product (disposable). Alternatively, it can be designated for repeat use.

In some embodiments, the orifice or opening to release the contents of the holding chamber is formed with a screw thread. The screw thread can be formed to connect to a tube (e.g., an intravenous drip tube), a hollow needle (cannula), a catheter, a three-way valve or similar. The screw thread can be formed as a standardised connecting system (particularly Luer-Lock).

In some embodiments, the movable section of the dosing apparatus is connected to the movable piston of the holding chamber or designed for one such connection.

The movable section is shaped as a handle in specific embodiments.

The positioning element and/or the device according to the present invention is or respectively are in specific embodiments according to the present invention connected to the movable section of the dosing apparatus or at least designed for such a connection.

The connection between the positioning element and/or the device according to the present invention on the one side and the movable section on the other side can be designed to be detachable or non-detachable.

The positioning element can cause the movable section to move with the help of, for example, a carrier or by means of an appropriate connection. By this means for example, the piston of the holding chamber can be moved by means of the positioning element in order to release the contents of the holding chamber through the orifice.

In some embodiments according to the present invention, the positioning element is connected to a motor, e.g., a stepper motor, a drive or actuating device, to which a controller or control system can be interfaced.

In specific embodiments according to the present invention the cable is connected to the electrical component of the dosing apparatus or features the electrical component.

An electrical component can be a sensor, a circuit, an optical-coupler or similar.

In some embodiments, the device according to the present invention is over its entire length or in at least a section thereof, a cable conduit.

In specific embodiments, the device according to the present invention exhibits over its entire length or in at least a section thereof, a round, square, oval or any other cross-sectional form, particularly a closed cross-sectional form.

The device according to the present invention can be manufactured from plastic, metal, fibre-reinforced material or other materials or feature such.

The device according to the present invention can be straight and/or have single or multiple bends or can have another form.

In specific embodiments, the device according to the present invention is connected so as to move together with the movable section of the dosing apparatus, or designed for one such a connection.

In some embodiments, the device according to the present invention is connected to the movable section in a type of carrier function. A carrier function can, for example, be a non-permanent positive fitting connection, e.g., constructed as a pin or ring on the device according to the present invention such that, e.g., by a linear movement of the movable section, the device will be carried along with it.

In specific embodiments of the invention, the device according to the present invention is connected permanently to the movable section of the dosing apparatus, or designed for such a connection.

The term permanent in these embodiments of the present invention denotes a limited or unlimited period of time.

A limited period of time can amount to, for example, one day, several days, weeks, months or years.

A limited period of time can, for example, add up to from commissioning to a next service date. A limited period of time can also be from the first installation of an electrical component and with this the first use of the cable in the dosing apparatus, until the exchange or replacement of these components at a later point in time.

A permanent connection can be formed so as to be detached again or non-detachable. A detachable connection is achievable for example by means of a plug-in (e.g., press-fit) of the device in the movable section of the dosing apparatus, a screw fit, or a detachable adhesive.

A connection can be sealed against liquids or gases using methods known to a person skilled in the art.

In specific embodiments according to the present invention, the cable is connected to a sensor fixed in the dosing apparatus, which is designed and/or suitable to detect the presence and/or the position of at the least the movable section and/or the holding chamber within the dosing apparatus.

The sensor can be an active or passive sensor.

In some embodiments according to the present invention, the sensor is an ultrasonic sensor, an opto-electronic sensor, a capacitive sensor or another sensor type. Also sensors based on other measurement principles are encompassed according to the present invention, for example magnetic-inductive sensors. The section of the device according to the present invention or dosing apparatus to be detected can be suitably prepared or formed. So, for example, the holding chamber can include materials that can be detected with a magnetic-inductive sensor.

In some embodiments, according to the present invention, the checking of the location or position by means of the sensor is carried out through a comparison of the currently received sensor signals with reference signals.

In specific embodiments, the device according to the present invention is inserted into a connection aperture in the dosing apparatus or is designed to be so inserted.

In some embodiments according to the present invention, the connection aperture is positioned in a housing—or a section hereof—of the dosing apparatus.

In some embodiments according to the present invention, the connection aperture connects an interior of the dosing apparatus with an exterior of the dosing apparatus or the vicinity of it.

In specific embodiments according to the present invention, the connection aperture has a round cross-section wholly or at least in a section thereof. The cross-section can also however be oval or square or exhibit any other form.

In some embodiments, the device according to the present invention is pushed into the connection aperture of the dosing apparatus, or plugged in or otherwise inserted.

In specific embodiments according to the present invention, at least the device and/or the connecting aperture respectively are formed completely or in part thereof as a sleeve, or feature such.

In specific embodiments according to the present invention, a sleeve is a tube or a tube section.

Sleeves can, for example, be made from plastic or metal with the known advantages of these materials.

In specific embodiments of the present invention, the sleeve- or tube-formed connection aperture in the dosing apparatus is arranged in such a way or provided for such an arrangement that it extends out from the housing section in which the connection opening is positioned at least 20 mm, preferably at least 25 mm, further preferred 30 or 35 mm into the interior and/or out to the exterior of the dosing apparatus.

In some embodiments, the sleeve- or tube-formed connection in the dosing apparatus exhibits a length of 20 mm or 25 mm or 30 mm or 35 mm. The sleeve can also exhibit a length between these values or shorter than 20 mm or longer than 35 mm.

The lengths identified in the two preceding paragraphs are advantageous by virtue of, for example, that disinfection liquids cannot enter the interior of the dosing apparatus through the connection aperture. Greater lengths in some embodiments according to the present invention are not required for this.

In specific embodiments of the invention, the device according to the present invention is arranged or designed for the arrangement in which at least one section of the device according to the invention is arranged inside at least one section of the—for example sleeve-formed or not sleeve-formed—connection aperture so as to slide relative to this.

In some embodiments of the present invention, the materials of the device according to the present invention and the structure surrounding the connection aperture are chosen in such a way that both elements are low-friction or friction-optimised for a sliding motion against one another. Suitable material combinations are known to persons skilled in the art.

In specific embodiments of the invention, the device according to the present invention is arranged or designed for the arrangement to be totally or at least with one section of the device coaxially—or fundamentally coaxially—slidable within the connection aperture.

The treatment apparatus according to the present invention is in some embodiments a blood treatment apparatus, particularly a hemodialysis apparatus, a hemofiltration apparatus or a hemodiafiltration apparatus.

The method to enable or carry out detection of the position of a movable section encompasses in specific embodiments according to the present invention the arrangement of the device according to the present invention or a section thereof inside a connection aperture or inside a section of the connection aperture.

Specific embodiments of the present invention feature one or more of the hereafter stated advantages.

The present invention provides a device for guiding a cable in a medical dosing apparatus. In carrying out the operation of the dosing apparatus, the cable can advantageously be moved relative to this or a section thereof, without in this case being mechanically loaded, for example, in the area of its connection to a sensor or to the movable section of the dosing apparatus. The cable will not be damaged during its movement. Such damage could be kinking, damage from proximity to hot machinery parts, damage from sharp edges, damage from resting on moving parts, cable breakage or the like. Such damage will be advantageously prevented by the guidance of the cable together with the device according to the present invention.

Furthermore by way of example, a cable or conductor by means of which a movable component inside the dosing apparatus or an apparatus for another purpose can be provided with power or transmit a signal, may be guided to the outside without damage during use in order to, e.g., be connected to a power source or a signal receiver external to the device.

In specific embodiments of the invention, the penetration of dripping water (e.g., through a water ingress protection according to IPX1), disinfecting agents or other liquids to the interior of the dosing apparatus will be advantageously prevented. These advantageous properties in specific embodiments according to the present invention result from the length of the connecting aperture; in some embodiments by virtue of a narrow gap between the device according to the present invention and the connecting aperture (this is valid especially when the device according to the present invention is arranged coaxially in the connecting aperture). Thus can internal electrical components such as sensors be protected from moisture.

The device according to the present invention can be a low priced commercially available tube or can likewise be produced economically as an injection moulded part.

The cable can be installed simply into the device according to the present invention in that it can be pulled through or inserted into it. In the inside of the device according to the present invention the cable is advantageously protected from damage from external effects or through catching on components of the dosing apparatus as well as through mechanical stress from other causes. In doing so, elaborate cable routing can advantageously be dispensed with.

The cable that is guided in the device according to the current invention, during movement of the movable section of the dosing apparatus, requires no—or at least little—movement of the cable relative to the device according to the present invention, given that the cable is slid or moved together with the device. This also constitutes a protection from mechanical stress of the cable.

The present invention will be exemplarily explained in the following with the help of the accompanying drawings in which identical reference numerals refer to similar or identical components. In the partly simplified representations, it applies:

FIG. 1 shows in partial longitudinal section a medical dosing apparatus (100) with a device (1) according to the present invention for guiding a cable (3).

The device (1) of FIG. 1 is shown exemplarily as a first sleeve or tube. This is in the upper area hereof guided in a connection aperture (5) embodied as a second sleeve or tube. The connection aperture (5) connects the inner area of the dosing apparatus (100) with the outside of the dosing apparatus (100).

By virtue of the length of the connection aperture (5) on the one side and the narrow gap between connection aperture (5) and device (1) on the other side, in the example of FIG. 1, the ingress of dripping water, disinfecting agents, or other liquids to the inside of dosing apparatus (100) will be advantageously prevented.

The lower end of the device (1) according to the present invention (relative to the embodiment in FIG. 1), is connected to a handle (300)-shaped movable section of the dosing apparatus (100). The lower end of the device (1) is open to the inside of the handle (300). Thus the cable (3) which is connected to a sensor (7) arranged in the handle (300) can be inserted in the device (1) according to the present invention from beneath. The cable (3) can be guided to the exterior together with the device (1) according to the present invention through the second tube- or sleeve-formed connection aperture (5).

The sensor (7) is designed in this application example to detect a syringe plunger (9) of a syringe (200) on the handle (300). Thus, the presence, the intended position of the syringe (200) in the dosing apparatus (100) and/or the position of the syringe plunger (9) relative to the syringe (200) or to the dosing apparatus (100) can be detected.

A clamping device (13) (of which in FIG. 1 only one part of the in principle two-part clamping device is shown) fixes the syringe plunger (9) in the handle (300).

A positioning element (11) is connected to the handle (300). The positioning element (11) is intended to move the handle (300) and with it the syringe plunger (9) with the object of dispensing substances or solutions held within the syringe (200). The positioning element (11) can be connected to a motor, for instance a stepper motor, e.g., at the upper end of the positioning element (11). By means of a suitable motor controller, a pre-determined quantity or rate of medication can be dispensed from the syringe.

When or if the positioning element (11) moves forward (in FIG. 1 in an upwards direction), the syringe plunger (9), the device (1) for guiding the cable (3) in addition to the handle (300) will be moved together with the positioning element (11).

Figure 2:
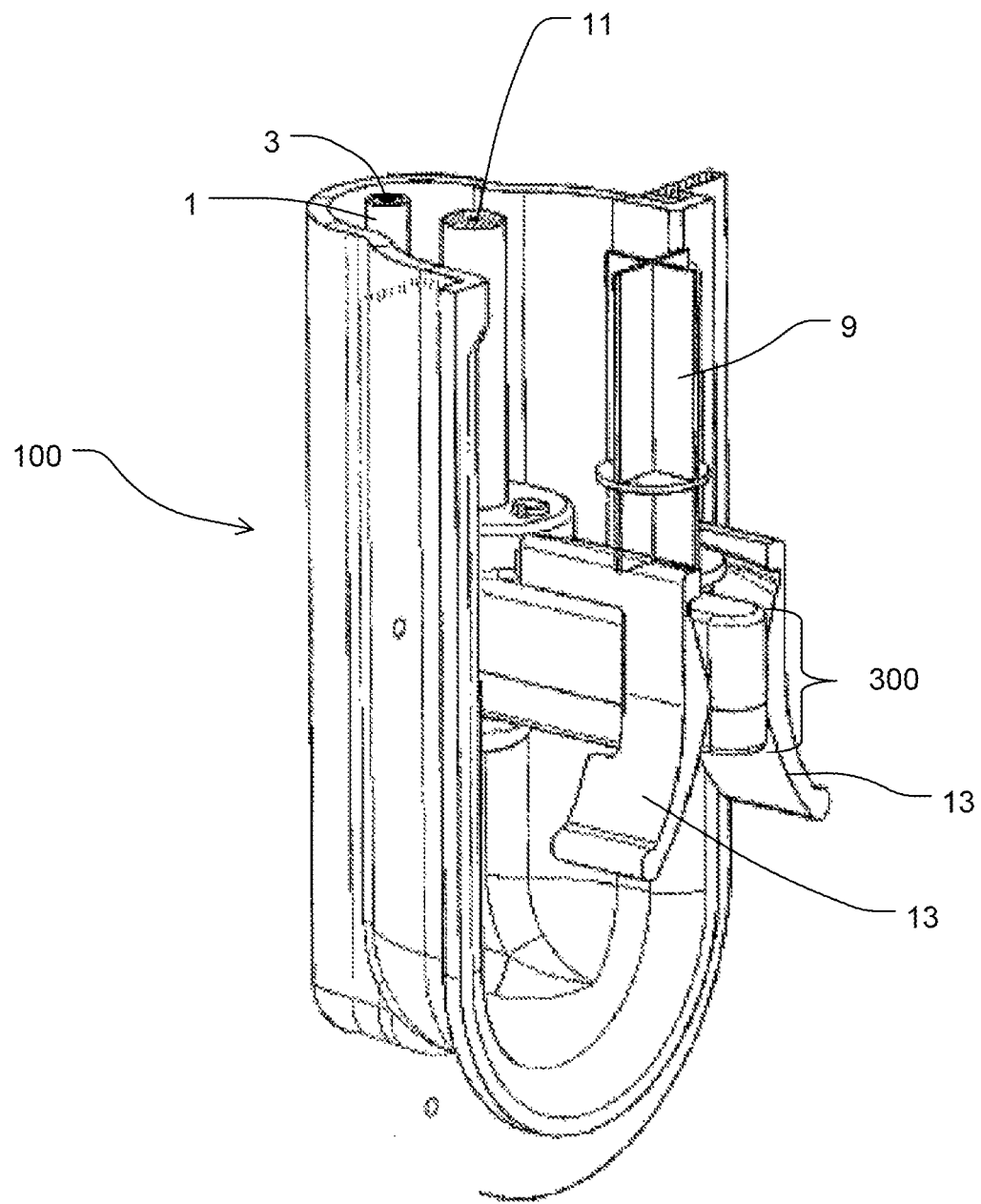
FIG. 2 shows a further sectional view of the dosing apparatus of FIG. 1.

FIG. 2 shows a cross-sectional view of the dosing apparatus (100) of FIG. 1. The cross section plane lies in the area of the syringe plunger (9).

The cross-section of the cable (3) is shown inside the device (1).

The connection aperture (5) not shown in FIG. 2, however, is attached above the section plane.

The clamping device (13) fixes the syringe plunger (9) in the handle (300) from two sides.

Figure 3:
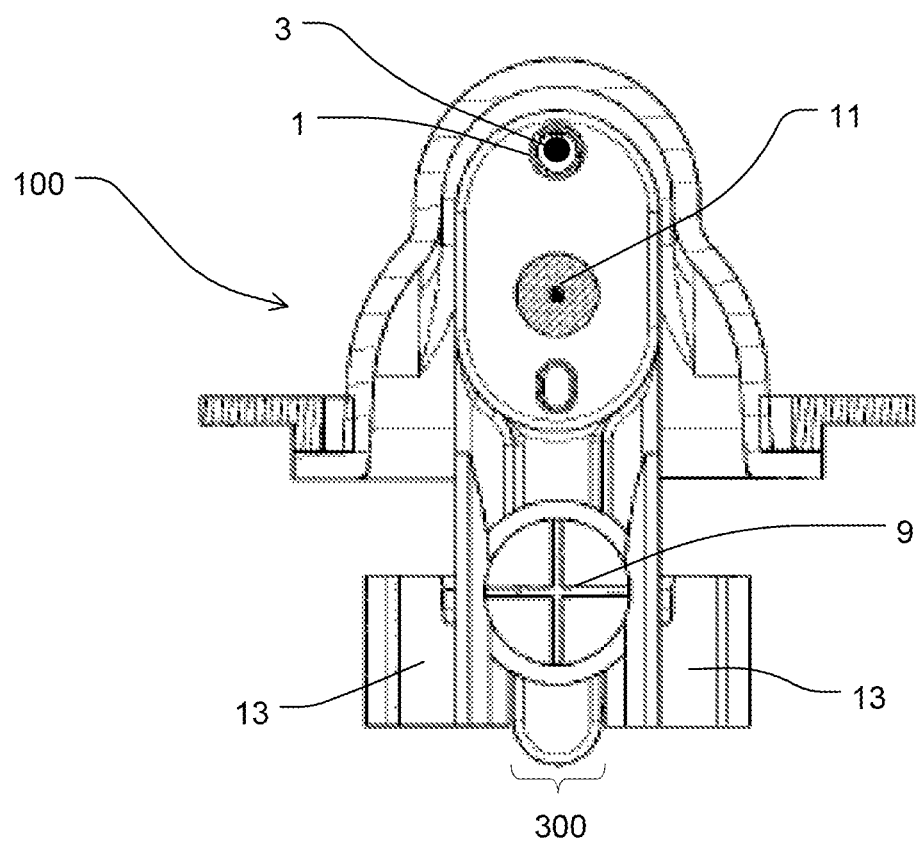
FIG. 3 shows another view of the section shown in FIG. 2 of the dosing apparatus according to the present invention of FIG. 1.

FIG. 3 shows the section of the dosing apparatus (100) according to the present invention of FIG. 2 in a two-dimensional view from above (relative to the view in FIG. 2).

The cross-section plane corresponds to that shown in FIG. 2 but is however shown in a plan view here.

Figure 4:
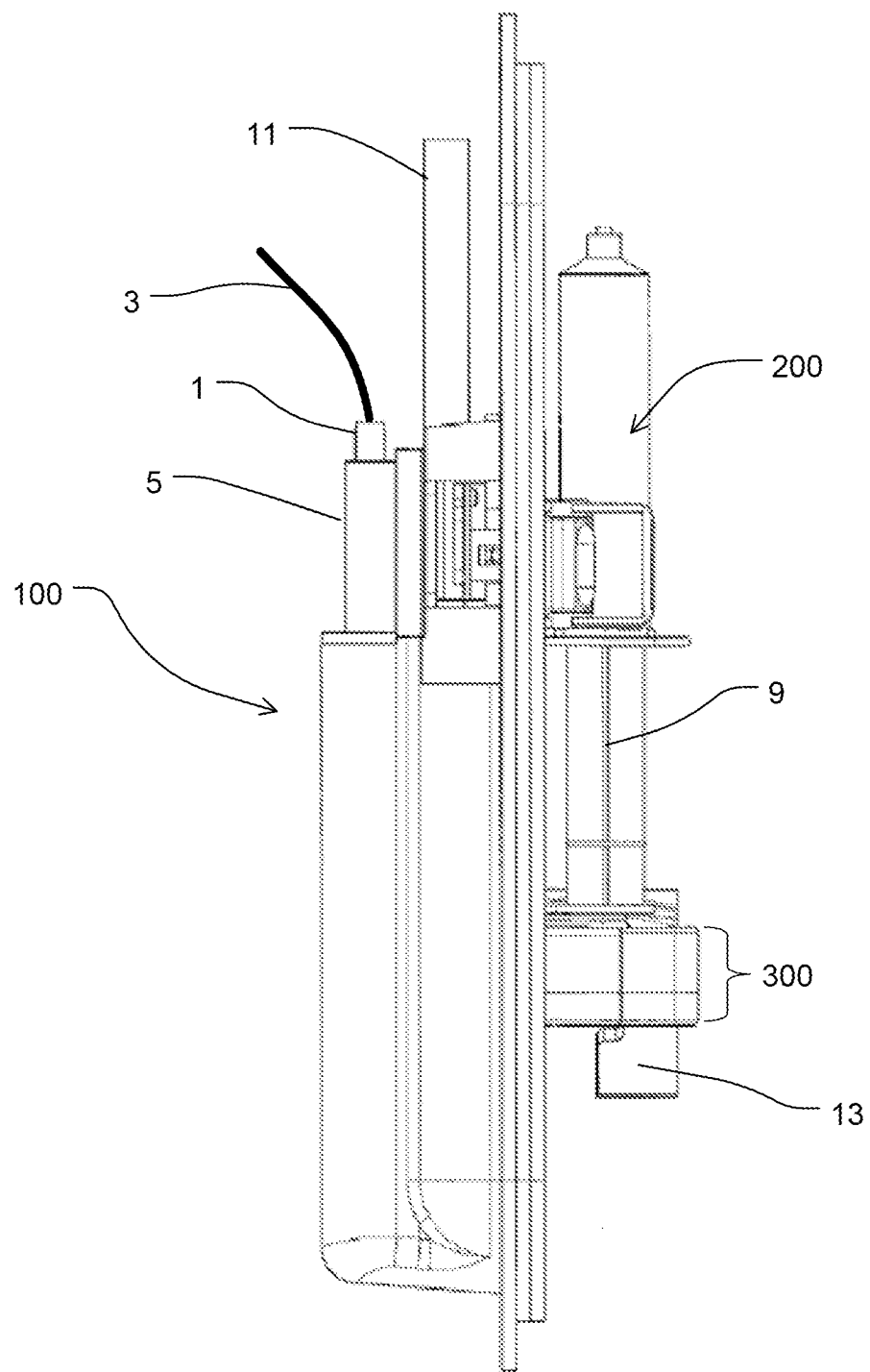
FIG. 4 shows a side view of the dosing apparatus of FIG. 1.

FIG. 4 shows an un-sectioned side view of the dosing apparatus (100) of FIG. 1.

From the device (1) according to the present invention, the cable (3) is guided out to the exterior of dosing apparatus (100). The device (1) according to the present invention is in turn inserted through the tube-formed connection aperture (5) and rises out from the interior of the dosing apparatus (100). The device (1) according to the present invention is arranged to be slidable within the connection aperture (5).

During operation of the dosing apparatus (100), the following parts and respectively sections will be moved upwards (relative to the view in FIG. 4): the syringe plunger (9), the handle (300), the clamping device (13), the device (1) according to the present invention (guided in the connection aperture (5) which is fixed to the housing of the dosing apparatus (100) and the cable (3) guided in the device (1).

Reference numeral list

| Reference numeral | Description |
|---|---|
| 100 | medical dosing apparatus |
| 200 | syringe with plunger, as holding chamber |
| 300 | handle, as movable section |
| 1 | device for guiding a cable |
| 3 | cable |
| 5 | connection aperture |
| 7 | sensor |
| 9 | syringe plunger |
| 11 | positioning element |
| 13 | clamping device |

The invention claimed is:

1. A dosing apparatus for a medical application, comprising:
a support device for at least one holding chamber for a substance or a solution to be dosed, wherein the at least one holding chamber is embodied as a variable volume syringe;
at least one cable or conductor;
a guiding device configured as a conduit for guiding the at least one cable or conductor; and
at least one movable section,
wherein the guiding device is connected, or configured to be connected, to the at least one movable section such that the guiding device is movable or configured to be moveable with the at least one movable section, and
wherein the movable section is configured to at least one of receive or connect to a movable piston of the at least one holding chamber.

2. The dosing apparatus according to claim 1, wherein the guiding device is non-detachably connected to the movable section or is configured to be detachably connected to the movable section.

3. The dosing apparatus according to claim 1, further comprising:
a sensor, wherein the at least one cable is connected to the sensor positioned in the dosing apparatus, wherein the sensor is configured to at least one of:
detect a position inside the dosing apparatus of at least one of the at least one movable section of the dosing apparatus or the holding chamber for the substance or the solution to be dispensed, or
detect a presence of the holding chamber within the dosing apparatus.

4. The dosing apparatus according to claim 1, wherein the guiding device is inserted or configured to be inserted in a connection aperture of the dosing apparatus, wherein the connection aperture is arranged in a section of a housing of the dosing apparatus, and an interior of the dosing apparatus is connected via the connection aperture with an exterior of the dosing apparatus.

5. The dosing apparatus according to claim 4, wherein at least one of the guiding device or the connection aperture is formed as a sleeve or includes a sleeve.

6. The dosing apparatus according to claim 5, wherein the sleeve-formed connection aperture is arranged in the dosing apparatus, or configured to be arranged in the dosing apparatus for extending at least 20 mm from the housing section in which the connection aperture is positioned into at least one of the interior or out the exterior of the dosing apparatus.

7. The dosing apparatus according to claim 6, wherein the sleeve-formed connection aperture is arranged for extending at least 25 mm from the housing section in which the connection aperture is positioned into at least one of the interior or out the exterior of the dosing apparatus.

8. The dosing apparatus according to claim 7, wherein the sleeve-formed connection aperture is arranged for extending 30 or 35 mm from the housing section in which the connection aperture is positioned into at least one of the interior or out the exterior of the dosing apparatus.

9. The dosing apparatus according to claim 5, wherein the guiding device, or at least one section thereof, is arranged in, or configured to be arranged for being slidable within, at least one section of the connection aperture and relative to the connection aperture or relative to the section thereof.

10. The dosing apparatus according to claim 9, wherein the guiding device, or at least one section thereof, is arranged in, or configured to be arranged for being coaxially or substantially coaxially slidable within, the connection aperture.

11. A treatment apparatus, comprising or being connected to the at least one dosing apparatus according to claim 1.

12. The treatment apparatus of claim 11, wherein the treatment apparatus is a blood treatment apparatus configured to administer hemodialysis, hemofiltration, or hemodiafiltration to a patient.

13. The dosing apparatus according to claim 1, further comprising:

a positioning element configured to move the movable section of the apparatus.

14. The dosing apparatus according to claim 1, wherein the holding chamber includes a cavity and the movable piston is configured to output a content of the holding chamber via a movement of the piston.

15. The dosing apparatus according to claim 1, wherein the conduit has a closed cross sectional configuration which houses the at least one cable or conductor.

* * * * *